(12) United States Patent
Osumi et al.

(10) Patent No.: US 7,387,783 B2
(45) Date of Patent: *Jun. 17, 2008

(54) KERATOTIC PLUG REMOVER

(75) Inventors: Takahiro Osumi, Hannan (JP);
Yasuyuki Murase, Yoshikawa (JP)

(73) Assignee: Kao Corporation, Tokyo (JP)

( * ) Notice: Subject to any disclaimer, the term of this patent is extended or adjusted under 35 U.S.C. 154(b) by 296 days.

This patent is subject to a terminal disclaimer.

(21) Appl. No.: 10/888,587

(22) Filed: Jul. 12, 2004

(65) Prior Publication Data

US 2004/0241136 A1 Dec. 2, 2004

Related U.S. Application Data

(63) Continuation of application No. 09/986,538, filed on Nov. 9, 2001, which is a continuation of application No. PCT/JP00/03026, filed on May 11, 2000.

(30) Foreign Application Priority Data

May 12, 1999 (JP) ................................. 11-131046

(51) Int. Cl.
*A61K 8/02* (2006.01)
*A61K 31/74* (2006.01)
*A01N 25/24* (2006.01)
*A01N 25/34* (2006.01)
*A61F 13/00* (2006.01)

(52) U.S. Cl. ...................... 424/401; 424/402; 424/443; 424/445; 424/449; 424/77; 424/78.03

(58) Field of Classification Search ................ 424/401, 424/443, 445
See application file for complete search history.

(56) References Cited

U.S. PATENT DOCUMENTS

| | | | | |
|---|---|---|---|---|
| 5,512,277 A | * | 4/1996 | Uemura et al. | 424/78.03 |
| 6,221,382 B1 | * | 4/2001 | Ishida et al. | 424/443 |
| 6,228,487 B1 | * | 5/2001 | Howard et al. | 428/355 CN |
| 6,602,513 B2 | * | 8/2003 | Mochizuki et al. | 424/401 |
| 6,723,667 B1 | * | 4/2004 | Saito et al. | 442/123 |
| 2004/0009140 A1 | * | 1/2004 | Nishijima et al. | 424/70.13 |

FOREIGN PATENT DOCUMENTS

| EP | 0 514 760 A1 | * | 11/1992 |
|---|---|---|---|
| WO | WO 9842302 A1 | * | 10/1998 |

OTHER PUBLICATIONS

U.S. Appl. No. 09/515,325, filed Feb. 29, 2000, Osumi et al.
U.S. Appl. No. 10/888,587, filed Jul. 12, 2004, Osumi et al.

* cited by examiner

*Primary Examiner*—S. Tran
(74) *Attorney, Agent, or Firm*—Oblon, Spivak, McClelland, Maier & Neustadt, P.C.

(57) ABSTRACT

The invention relates to a keratotic plug remover comprising, as active ingredients, (A) a polymer having sulfonic or sulfate groups or having salts thereof and (B) a nonionic polymer, and a pack for pores of the skin containing said remover. The use of the pack for pores of the skin permits cleanly keeping the skin and pores of the skin and suppressing the conspicuousness of pores of the skin because the strength of a film formed therefrom is high even under high humidity, and so the film is easy to peel, and keratotic plugs filled in the pores of the skin can be removed with high reliability.

21 Claims, 1 Drawing Sheet

KERATOTIC PLUG REMOVER

BACKGROUND OF THE INVENTION

1. Field of the Invention

The present invention relates to a keratotic plug remover, a sheet-like pack for pores of the skin and a method of removing keratotic plugs

2. Discussion of the Background

Various troubles can be caused on the skin by smears on the skin, such as sebum and keratotic plugs. In particular, keratotic plugs are smears keratinized together with sebum and which are filled in pores of the skin and form the cause that the pores of the skin become conspicuous. Therefore, it is preferred from the viewpoint of the healthy function and aesthetic appearance of the skin that keratotic plugs which are filled in the pores of the skin be removed.

A film type pack composition making good use of a water-soluble polymer such as polyvinyl alcohol as a film-forming agent, and a film type pack composition described in Japanese Patent Application Laid-Open No. 255041/1993, making good use of an aqueous resin emulsion as a film-forming agent have heretofore been used for the purpose of removing dirt or smears on the skin. A keratotic plug remover described in Japanese Patent Application Laid-Open No. 97627/1993, by which keratotic plugs can be removed with good results, and the like have been used for the purpose of removing keratotic plugs in particular.

However, the conventional film type pack compositions cannot achieve any sufficient effect on the removal of the keratotic plugs, while the keratotic plug remover described in Japanese Patent Application Laid-Open No. 97627/1993 has a high effect of removing the keratotic plugs. However, the strength of a film formed therefrom is lowered under high humidity, so that the film is hard to peel, and its keratotic plug-removing effect is lowered.

Keratotic plug removers are described by Uemura et al. in U.S. Pat. Nos. 5,512,277 and 6,306,328.

It is an object of the present invention to provide a keratotic plug remover by which the film strength thereof is high, and keratotic plugs filled in pores of the skin can be removed with high reliability, and a pack for pores of the skin making use of this remover.

SUMMARY OF THE INVENTION

The present invention provides a keratotic plug remover comprising, as active ingredients, (A) a polymer (hereafter referred to as Polymer (A)) having sulfonic or sulfate groups or having salts thereof; and (B) a nonionic polymer (hereafter referred to as Polymer (B)); a sheet-like pack for pores of the skin, comprising Polymer (A) and Polymer (B); and a process for removing keratotic plugs.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
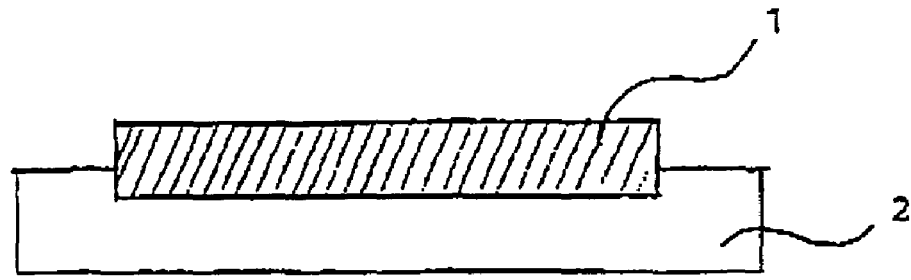
FIG. 1 illustrates a cross section of a sheet-like pack according to the present invention.

Examples of Polymer (A) used in the present invention include the following polymers (a) to (d):

(a) homopolymers of a vinyl monomer (hereafter referred to as Vinyl Monomer (a)) having a (meth)acryloyl skeleton or styrene skeleton and a sulfonic or sulfate group, or a salt thereof (hereafter referred to as an acidic group);

(b) copolymers of Vinyl Monomer (a) with a monomer copolymerizable therewith;

(c) polysaccharides containing the above acidic group, such as carboxymethyl cellulose, alginic acid and salts thereof; and (d) homopolymers of vinylsulfuric acid, vinylsulfonic acid, allylsulfonic acid or a salt thereof, or copolymers of such a monomer with a monomer copolymerizable therewith.

Examples of the monomer having a (meth)acryloyl skeleton include (a-1) (meth)acrylic acid, (a-2) monomers having a (meth)acrylate skeleton and (a-3) monomers having a (meth)acrylamide skeleton. (a-1) (Meth)acrylic acid is an example of the vinyl monomer having a carboxyl group. Examples of (a-2) the monomer having the acidic group and the (meth)acrylate skeleton include 3(meth)acryloyloxypropanesulfonic acid. Examples of (a-3) the monomer having the acidic group and the (meth)acrylamide skeleton include 2-(meth)acrylamido-2-methylpropanesulfonic acid. Examples of the monomer having the acidic group and the styrene skeleton include styrenesulfonic acid.

When Polymer (A) is a copolymer, it is preferred that the content of the vinyl monomer having an acidic group be at least 20 mol % based on all monomers used in the preparation of the copolymer from the viewpoint of the keratotic plug-removing effect of the resulting keratotic plug remover. No particular limitation is imposed on a comonomer for copolymerization with the vinyl monomer havint an acidic group, so far as it is a comonomer which is copolymerizable therewith.

The salt of the acidic group in Polymer (A) may be neutralized to any degree of neutralization with a basic substance and may be neutralized to a specific degree of 5%, 10%, 15%, 20%, 25%, 30%, 35%, 40%, 45%, 50%, 55%, 60%, 65%, 70%, 75%, 80%, 85%, 90%, 95% and 100%, based on the total amount of acidic groups in Polymer (A). Examples of a cationic ion at this time include alkali metal ions, alkaline earth metal ions, an ammonium ion and alkylammonium ions. Such a salt may be formed either at the point of time of its corresponding monomer or after the preparation of the polymer.

Examples of Polymer (B) include the following polymers (e) to (g):

(e) homopolymers of a vinyl monomer (hereafter referred to as Vinyl Monomer (b)) having an amide group;

(f) copolymers of Vinyl Monomer (B) with a monomer copolymerizable therewith; and (g) polyethylene glycol, polypropylene glycol, polyglycerol, polyvinyl alcohol, pullulan, guar gum, hydroxyethyl cellulose and the like.

Examples of polymers belonging to the polymers (e) to (g) include polyvinyl pyrrolidone, vinylpyrrolidone-vinyl acetate copolymers, poly(N,N-dimethylacrylamide), poly(N-vinylacetamide), poly(N-vinylformamide) and poly(2-alkyl-2-oxazoline).

Polymer (B) may contain an ionic group in a proportion of at most 10 mol % based on the whole monomer so far as a nonionic component is contained as a main component. As an examples of a nonionic polymer having an ionic group, may be mentioned carboxy-modified polyvinyl alcohol.

Combinations of Polymer (a) with Polymer (e), Polymer (a) with Polymer (f), polymer (b) with Polymer (e), and Polymer (b) with Polymer (f) are preferred from the viewpoint of the keratotic plug-removing ability of the resulting remover. Among these combinations, the combination of Polymer (a) with Polymer (e) is more preferred.

As Polymers (A) and (B), one or more of the above-mentioned polymers may be respectively used. The weight average molecular weights of each polymer is independently preferably within a range of 10,000 to 3,000,000, with those having a weight average molecular weight of 100,000 to 1,000,000 being particularly preferred from the viewpoint of film strength and easy application.

The mixture of Polymers (A) and (B) used in the present invention may become turbid when they are dissolved in water, but are preferably soluble in water from the viewpoints of the effect of removing keratotic plugs and appearance. The nature "water solubility" in the present invention can be identified by the fact that the transmittance of a mixture prepared by uniformly mixing 1 part by weight of the copolymer with 99 parts by weight of ion-exchanged water is at least 95% when the mixture is placed in a quartz cell (optical path length: 1 cm) to measure its transmittance at a light wavelength of 370 nm by means of a general spectrophotometer for ultraviolet and visible region (for example, UV-265FW manufactured by Shimadzu Corporation).

Polymers (A) and (B) are typically present as a polymer blend.

A mixing proportion of Polymer (A) to Polymer (B) in the keratotic plug remover and pack for pores of the skin according to the present invention is preferably 5:95 to 95:5, more preferably 30:70 to 70:30 in terms of a weight ratio of (A) to (B) from the viewpoint of the keratotic plug-removing ability. As examples of a method for mixing these polymers, may be mentioned a method in which the respective polymers are dissolved in separate proper solvents, and the resultant solutions are mixed with each other, and a method in which both components are dissolved at once in a proper solvent.

Polymers (A) and (B) may be incorporated in a proportion of 0.01 to 100% by weight in total into the keratotic plug remover according to the present invention. Incidentally, no limitation is imposed on the residual components such as a solvent so far as no detrimental influence is thereby imposed on the ability to remove keratotic plugs.

The total content of Polymers (A) and (B) in the pack for pores of the skin according to the present invention is preferably controlled to 1.0 to 99.9% by weight, more preferably 20 to 95% by weight.

Each of Polymers (A) and (B) is generally dissolved in a solvent before use. The solvent may be any solvent so far as it can stably dissolve the polymer therein. For example, one of water, ethyl alcohol, isopropyl alcohol and the like or any combination thereof may be used. The content of the solvent may be suitably adjusted according to Polymers (A) and (B), other optional components and the form of the composition. However, the content is preferably 0.1 to 99.0% by weight, more preferably 1 to 80% by weight based on the pack for pores of the skin.

Into the keratotic plug remover according to the present invention, components commonly used in the classical cosmetic compositions, for example, the components described in Japanese Patent Application Laid-Open No. 97627/1993, page 19, lines 2 to 38, may be incorporated in addition to Polymers (A) and (B). Among these components, any of polyhydric alcohols such as ethylene glycol, diethylene glycol and still higher polyethylene glycols; propylene glycol, dipropylene glycol and still higher polypropylene glycols; butylene glycols such as 1,3-butylene glycol; glycerol, diglycerol and still higher polyglycerols; sugar alcohols such as sorbitol; adducts of glycerols with ethylene oxide (hereafter referred to as EO) and propylene oxide (hereinafter referred to as PO); EO-PO adducts of sugar alcohols; EO-PO adducts of monosaccharides; and EO-PO adducts of polysaccharides is incorporated for the purpose of adjusting the strength of a film formed. These polyhydric alcohols are preferably contained in a proportion of 0.01 to 50% by weight in the keratotic plug remover.

Powder, such as inorganic powder such as titanium oxide, zinc oxide, silica, alumina, calcium carbonate, calcium silicate, mica, talc or kaolin, or powder of an organic polymer such as nylon, cellulose or a polystyrene resin may be contained for the purpose of controlling the strength of a film formed and drying property. These powders are preferably contained in a proportion of 1 to 50% by weight in the the keratotic plug remover.

When any of oily components, such as hydrocarbons such as liquid paraffin, squalane, vaseline and solid paraffin; natural oils; ester oils; silicone oils; and higher fatty acids is contained into the keratotic plug remover, the peel strength of a film formed after the keratotic plug remover is dried can be adjusted, so that the film can be peeled from the skin without irritating the skin. These oily components are preferably incorporated in a proportion of 0.01 to 10% by weight in the keratotic plug remover. In order to enhance the shelf stability of the resulting keratotic plug remover, a surfactant may be contained in a proportion of 0.01 to 5% by weight in the keratotic plug remover.

Besides, additives such as coloring matter, vitamins, anti-inflammatory agents, germicides, preservatives, ultraviolet absorbents, whitening agents and moisturizers may be contained.

The keratotic plug remover according to the present invention may be of the type that it is dried once to remove a solvent therefrom, and it is dissolved again in a solvent right before its use to use it. In order to remove keratotic plugs, the pack for pores of the skin according to the present invention may be used by coating or plastering the skin, at which keratotic plugs are present, therewith, drying it and then peeling it from the skin.

The keratotic plug remover according to the present invention may be used in the form of either the ordinary peel-off type that there is no need to use a support or a sheet-like pack that Polymers (A) and (B) are applied to a support. Alternatively, it may be used by coating the skin with a paste containing Polymers (A) and (B) and then covering the coated portion with a support. As the support used herein, is preferred a water vapor-permeable support such as a fabric or nonwoven fabric made of one or at least two selected from natural fibers such as cotton, hemp and wool; regenerated cellulose type fibers such as rayon and acetate; and chemical fibers composed of polyester, polyurethane, polyamide, polypropylene, polyethylene or the like.

The sheet-like pack according to the present invention is composed of a cosmetic composition comprising Polymers (A) and (B) and a water vapor-permeable support. A specific preferable example thereof includes a pack in which a cosmetic composition 2 containing the keratotic plug remover is supported on a water vapor-permeable support 1 as illustrated in FIG. 1 in such a manner that the water vapor-permeable support 2 forms a surface of the sheet-like pack.

In the sheet-like pack according to the present invention, the cosmetic composition 2 containing the keratotic plug remover may be either in the form of a paste (generally, solvent content: 20 to 95% by weight) having flowability or in a dry state generally, solvent content: 1 to 80% by weight) having no flowability.

The sheet pack including the cosmetic substance in a paste-like state generally has a water content of 30 to 80% by weight and a thickness of 50 to 2000 μm whereas the sheet pack including the cosmetic substance in a dry state generally has a water content of 0.1 to 30%, preferably 15 to 20% by weight and a thickness of 10 to 1000 μm. In sheet-pack is provided with a layer of polymer in an amount sufficient to effectively remove keratotic plugs, the specific amount of which may vary depending on the specific polymer mixture used. The determination of an amount of polymer effective to remove ketatotic plugs is within the level of skill of those of ordinary skill in the art, without undue experimentation.

A sheet-like pack is composed of the cosmetic composition containing the keratotic plug remover and the water vapor-permeable support as described above. However, a release sheet which is separated and removed upon use may be laminated on the surface on the side of the cosmetic composition as needed. Examples of such a release sheet include sheets formed of polyester, polypropylene, polyethylene, nylon and the like. A suitable support layer is described in U.S. Pat. No. 6,221,382, the relevant portions of which, which describe the support layer, are hereby incorporated by reference.

No particular limitation is imposed on the external form of the sheet-like pack, and it may be formed into a sheet having a predetermined width and suitably cut out for use upon application to the skin. Alternatively, it may be cut out in advance into forms suitable for application to parts such as forehead, cheek and nose, at which dirt or smears in pores of the skin are present in plenty. In a preferred embodiment the sheet-like pack is provided in a form in which an upper edge comprises a receding portion and a lower edge comprises a projecting portion, wherein the receding portion and the projecting portion are fittable with each other. A suitable shape is described in U.S. Pat. No. 6,299,605, the relevant portions of which, which described the shape of the sheet pack, are hereby incorporated by reference.

As a method for using the sheet-like pack, is preferred a method in which the sheet-like pack is applied to the skin as it is, or the side of the cosmetic composition containing the keratotic plug remover of the sheet-like pack is applied to the skin after water is supplied to at least one of the skin and the side of the cosmetic composition of the sheet-like pack, the cosmetic composition of the sheet-like pack is dried, and the whole sheet-like pack is then peeled from the skin.

EXAMPLES (1) Evaluation of Film Strength:

An aqueous solution containing Polymers (A) and (B) in a proportion of 20% by weight in total was prepared, and the solution was developed on a Teflon-made Petri dish and dried at 25° C. to form a film having a thickness of about 400 μm. After the film was cut into a rectangle of 3 cm×0.5 cm so as not to crack it, the resultant film specimen was left to stand for 2 days in an atmosphere of 58% RH (relative humidity) or 81% RH. The thus-treated film specimen was subjected to a tensile test under measuring conditions of strain of 0.01%, frequency of 10 Hz, a ratio of static stress to dynamic stress of 2.5 and 25° C. by means of a general dynamic viscoelastometer (for example, DVA-200 manufactured by IT Keisoku Seigyo K.K.) to measure its storage elastic modulus E'. The strength of the film was ranked as ⊙ where E' was at least 5×10$^8$ Pa, ○ where E' was not lower than 1×10$^7$ Pa, but lower than 5×10$^8$ Pa, Δ where E' was not lower than 1×10$^6$ Pa, but lower than 1×10$^7$ Pa, or x where E' was lower than 1×10$^6$ Pa.

(2) Evaluation of the Ability to Remove Keratotic Plugs:

(A) Type Coated on the Skin (Pasty Pack)

A mixture of Polymers (A) and (B) was used to prepare a pack for pores of the skins in accordance with the formulation shown in Table 1. The pack for pores of the skins was coated on the nose of a panelist after washing her face in a proportion of 0.1 mL/cm$^2$, left to stand for 30 minutes at 25° C. and 50% RH or 80% RH and then peeled from the nose. The measurement was conducted on the same panelist, and the evaluation under these two conditions was carried out at an interval of 1 week. A percent removal of keratotic plugs was then found in accordance with the following formula (I) to evaluate the pack for pores of the skin as to the ability to remove keratotic plugs. The pack for pores of the skin was ranked as ⊙ where the percent removal of keratotic plugs was at least 35%, ○ where the percent removal of keratotic plugs was not lower than 20%, but lower than 35%, Δ where the percent removal of keratotic plugs was not lower than 5%, but lower than 20%, or x where the percent removal of keratotic plugs was lower than 5%.

TABLE 1

| Polymers (A) and (B) | 20 (parts by weight) |
|---|---|
| Preservative | q.s. |
| Purified water | 80 |

(B) Type Plastered on the Skin (Sheet-like Pack)

A water vapor-permeable support and a mixture of Polymers (A) and (B) were used to prepare a sheet-like pack in accordance with the formulation shown in Table 2. A proper amount of water was first applied to a skin portion, on which the sheet-like pack will be plastered, and the sheet-like pack was plastered on this portion, dried at 25° C. and 50% RH or 80% RH and then peeled from the skin. The measurement was conducted on the same panelist, and the evaluation under these two conditions was carried out at an interval of 1 week. A percent removal of keratotic plugs was then found in accordance with the following formula (I) to evaluate the sheet-like pack as to the ability to remove keratotic plugs. The sheet-like pack was ranked as ⊙ where the percent removal of keratotic plugs was at least 35%, ○ where the percent removal of keratotic gs was not lower than 20%, but lower than 35%, Δ where the percent removal of keratotic plugs was not lower than 5%, but lower than 20%, or x where the percent removal of keratotic plugs was lower than 5%.

TABLE 2

| Polymers (A) and (B) | 20 (parts by weight) |
|---|---|
| Silicic anhydride | 16 |
| Glycerol | 6 |
| Preservative | q.s. |
| Purified water | 58 |

Percent removal of keratotic plugs=(the number of keratotic plugs attached to 1 cm$^2$ of pack)/(the number of keratotic plugs present in a region of 1 cm$^2$ on a wing of the nose)×100   (I)

Examples 1 to 10 and Comparative Examples 1 to 6 were taken as examples of (A), and Examples 11 and 12 and Comparative Examples 7 and 8 were taken as examples of (B) to evaluate their corresponding polymer compositions shown in Table 3.

TABLE 3

| Example | Polymer (A) | Polymer (B) | Polymer (A)/Polymer (B) (weight ratio) | Film strength 58% RH | Film strength 81% RH | Keratotic plug remover 50% RH | Keratotic plug remover 80% RH |
|---|---|---|---|---|---|---|---|
| Ex. 1 | PNaSS | PVP | 50/50 | ◎ | ○ | ◎ | ○ |
| Ex. 2 | PNaSS | PVP/VA | 40/60 | ◎ | ◎ | ○ | ○ |
| Ex. 3 | PNaSS | PVAAm | 55/45 | ◎ | ○ | ○ | ○ |
| Ex. 4 | PNaSS | PVA | 50/50 | ○ | ○ | ○ | ○ |
| Ex. 5 | PAMPSNa | PVP | 40/60 | ○ | ○ | ○ | ○ |
| Ex. 11 | PNaSS | PVP | 50/50 | ◎ | ○ | ◎ | ○ |
| Ex. 12 | PNaSS | PVA | 50/50 | ○ | ○ | ○ | ○ |
| Comp. Ex. 1 | PNaSS | — | 100/0 | ◎ | ○ | △ | △ |
| Comp. Ex. 2 | PVP | — | 100/0 | ○ | ○ | X | X |
| Comp. Ex. 3 | PQDM | PVP | 50/50 | ○ | X | ◎ | X |
| Comp. Ex. 4 | PMAA | — | 100/0 | ◎ | ○ | X | X |
| Comp. Ex. 5 | PVA | — | 100/0 | ○ | ○ | X | X |
| Comp. Ex. 6 | PQDM | PVA | 50/50 | ○ | X | ◎ | X |
| Comp. Ex. 7 | PNaSS | — | 100/0 | ◎ | ○ | ○ | △ |
| Comp. Ex. 8 | PQDM | — | 100/0 | ○ | X | ◎ | X |

PNaSS: Polystyrenesulfonic acid (PS-50, product of Toso Co., Ltd.)
PVP: Polyvinyl pyrrolidone (K-30, product of Wako Pure Chemical Industries, Ltd.)
PVP/VA: Vinylpyrrolidone-vinyl acetate copolymer (W-735, product of International Specialty Products Co.)
PVAAm: Poly(N-vinylacetamide) (weight average molecular weight: 270,000)
PVA: Polyvinyl alcohol (Gohsenol EG-30, product of The Nippon Synthetic Chemical Industry Co., Ltd.)
PAMPSNa: Poly(2-acrylamido-2-methylpropanesulfonic acid) (weight average molecular weight: 400,000)
PQDM: Polymethacryloyloxyethyltrimethylammonium chloride (weight average molecular weight: 270,000)
PMAA: Partial sodium salt of polyacrylic acid (neutralization: 55 mol %) (weight average molecular weight: 460,000)

INDUSTRIAL APPLICABILITY

The use of the pack for pores of the skin according to the present invention permits cleanly keeping the skin and pores of the skin and suppressing the conspicuousness of pores of the skin because the strength of a film formed therefrom is high even under high humidity, and so the film is easy to peel, and keratotic plugs filled in the pores of the skin can be removed with high reliability.

Obviously, numerous modifications and variations of the present invention are possible in light of the above teachings. It is therefore to be understood that within the scope of the appended claims, the invention may be practiced otherwise than as specifically described herein.

This application is based on Japanese patent application 11-131046 filed in the Japanese Patent Office on May 12, 1999, and WO 00/69397 filed with the Japanese receiving office of WIPO on May 11, 2000, the entire contents of each are hereby incorporated by reference.

What is claimed as new and desired to be secured by Letters Patent of the United States is:

1. A keratotic plug remover comprising:
   (i) a polymer (A) which is polystyrene sulfonic acid or a salt thereof; and
   (ii) a nonionic polymer (B) which is polyvinylpyrrolidone,
   wherein polymer (A) and nonionic polymer (B) are soluble in water, and a mixing proportion of said polymer (A) to nonionic polymer (B) is 30:70 to 70:30 in terms of a weight ratio of (A) to (B).

2. The keratotic plug remover according to claim 1, wherein the weight average molecular weight of polymer (A) and nonionic polymer (B) are each independently within a range of 10,000 to 3,000,000.

3. The keratotic plug remover according to claim 1, wherein the weight average molecular weight of polymer (A) and nonionic polymer (B) are each independently within a range of 100,000 to 1,000,000.

4. The keratotic plug remover of claim 1, further comprising a polyhydric alcohol.

5. The keratotic plug remover of claim 4, wherein said polyhydric alcohol is selected form the group consisting of ethylene glycol, diethylene glycol, polyethylene glycols; propylene glycol, dipropylene glycol, butylene glycols, glycerol, diglycerol, sugar alcohols, adducts of glycerols with ethylene oxide and propylene oxide, ethylene oxide-propylene oxide adducts of sugar alcohols, ethylene oxide-propylene oxide adducts of monosaccharides, and ethylene oxide-propylene oxide adducts of polysaccharides.

6. The keratotic plug remover of claim 1, further comprising a powder.

7. The keratotic plug remover of claim 6, wherein said powder is selected from the group consisting of titanium oxide, zinc oxide, silica, alumina, calcium carbonate, calcium silicate, mica, talc, kaolin, nylon powder, cellulose powder, a polystyrene resin powder and a mixture thereof.

8. The keratotic plug remover of claim 1, further comprising an oily component.

9. The keratotic plug remover of claim 8, wherein said oily component is selected from the group consisting of liquid paraffin, squalane, vaseline, solid paraffin, natural oils, ester oils, silicone oils, higher fatty acids and a mixture thereof.

10. The keratotic plug remover of claim 1, further comprising a surfactant in a proportion of 0.01 to 5% by weight in the keratotic plug remover.

11. The keratotic plug remover of claim 1, further comprising an element selected from the group consisting of a coloring matter, vitamins, anti-inflammatory agents, germicides, preservatives, ultraviolet absorbents, whitening agents, moisturizers and a mixture thereof.

12. A sheet pack comprising a cosmetic composition comprising the keratotic plug remover of claim 1 and a water vapor-permeable support.

13. The sheet pack of claim 12, wherein said keratotic plug remover has no flowability.

14. The sheet pack of claim 13, wherein said keratotic plug remover has a solvent content of from 1 to 80%.

15. The sheet pack of claim 12, wherein said keratotic plug remover has a water content of from 0.1 to 30%.

16. The sheet pack of claim 12, wherein said keratotic plug remover has a water content of from 15 to 20%.

17. A process for removing keratotic plugs, which comprises:
  i) coating or plastering skin with the keratotic plug remover of claim 1;
  ii) drying said keratotic plug remover; and
  ii) peeling said keratotic plug remover from said skin.

18. A process for removing keratotic plugs, which comprises plastering skin with a sheet pack comprising a cosmetic composition comprising the keratotic plug remover of claim 1 and a water vapor-permeable support; and
  ii) drying the pack; and
  iii) peeling said pack from said skin.

19. The process of claim 18, wherein said keratotic plug remover has no flowability further comprising wetting said skin or said sheet pack prior to plastering said skin.

20. The process of claim 19, further comprising wetting said skin prior to plastering said skin.

21. The process of claim 19, further comprising wetting said sheet pack prior to plastering said skin.

* * * * *